United States Patent [19]

Tjornehoj et al.

[11] Patent Number: 4,475,398

[45] Date of Patent: Oct. 9, 1984

[54] SUCCESSIVE APPROXIMATION ENVELOPE DETECTION FOR ESTIMATING THE AMPLITUDE OF A PLURALITY OF SUCCESSIVELY OCCURRING ELECTRICAL PULSES

[75] Inventors: David J. Tjornehoj, Longmont; Donald E. Dick, Boulder; Richard E. Kiefer, Boulder; Fred L. Smith, III, Boulder, all of Colo.

[73] Assignee: Armco Inc., Middletown, Ohio

[21] Appl. No.: 433,551

[22] Filed: Oct. 8, 1982

[51] Int. Cl.³ ............................................. G01N 29/02
[52] U.S. Cl. .................................... 73/599; 324/99 D
[58] Field of Search ......................... 73/599, 432 PS; 307/351, 362; 364/483; 324/99 D, 103 P

[56] References Cited

U.S. PATENT DOCUMENTS

| | | | |
|---|---|---|---|
| 2,845,597 | 7/1958 | Perkins | 324/103 P |
| 3,159,787 | 12/1964 | Sexton et al. | 324/123 R X |
| 3,703,002 | 11/1972 | Van Saun | 324/99 D X |
| 4,069,452 | 1/1978 | Conway et al. | 307/351 X |

Primary Examiner—James J. Gill
Attorney, Agent, or Firm—Frost & Jacobs

[57] ABSTRACT

The attenuation of RF pulses passing through a mineral slurry is determined by measuring the amplitude of the envelope produced by a series of successively occurring attenuated electrical pulses. The pulses are applied to the input of a variable gain amplifier, the gain of which is under control of a digital processor. The peak amplitude of each pulse is compared with a fixed reference voltage. The contents of a storage register associated with the processor is modified dependent upon whether the pulse amplitude is geater or less than the reference voltage. The contents of the register is used to control the gain of the variable gain amplifier in such a way that the amplitude of the next successive pulse will approach the value of the reference voltage. After the last pulse has been measured, the gain of the amplifier is inversely proportional to the amplitude of the pulse envelope, and the contents of the successive approximation register will also be proportional to the amplitude of the pulse envelope. The system may be calibrated using a precision attenuator to establish the degree of attenuation when no slurry is present.

20 Claims, 2 Drawing Figures

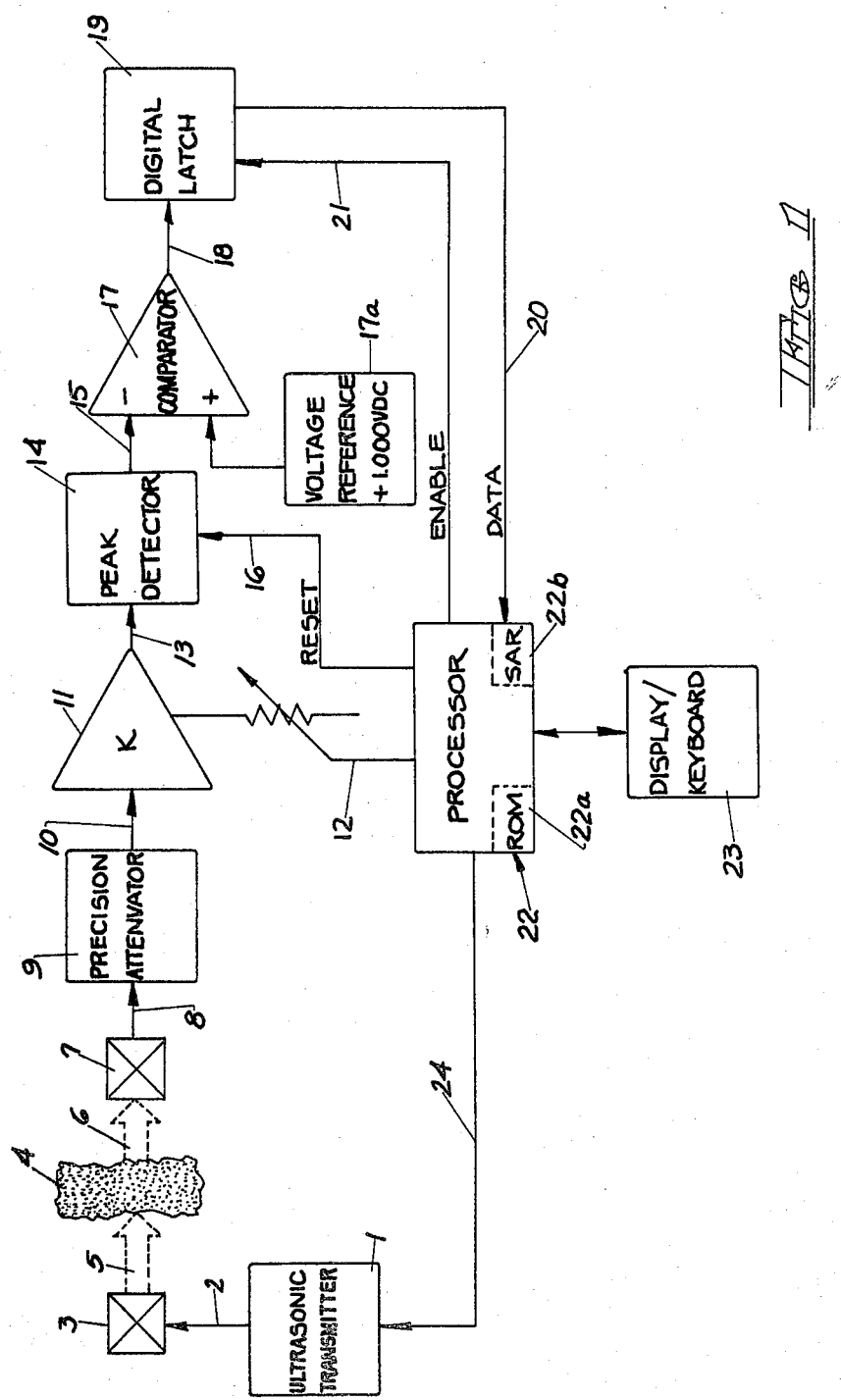

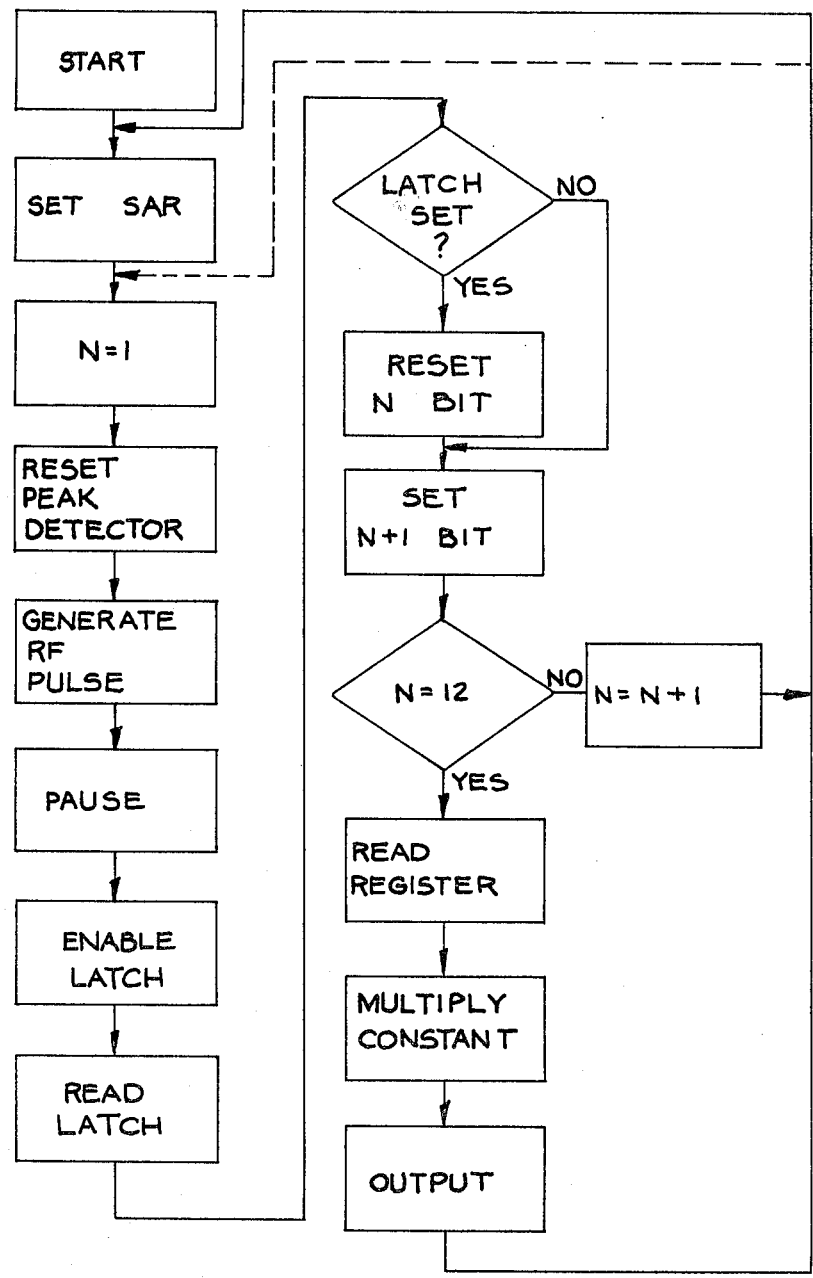

SUCCESSIVE APPROXIMATION ENVELOPE DETECTION FOR ESTIMATING THE AMPLITUDE OF A PLURALITY OF SUCCESSIVELY OCCURRING ELECTRICAL PULSES

SUMMARY OF THE INVENTION

The present invention is directed to apparatus for measuring the amplitude of the envelope produced by the peaks of a plurality of successively occurring electrical pulses, and more particularly to apparatus in which the amplitude of the received pulses is varied using digital processing by successively approximating the peak amplitude of successively occuring pulses to result in a value which is representative of the amplitude of the envelope formed by the pulse train.

The present invention finds particular application in measuring the amplitude of the envelope of electrical pulses resulting from the measurement of the attenuation of ultrasonic RF energy passing through a mineral slurry. In this application, an ultrasonic transmitter sends spaced pulses of known amplitude through a thin layer of mineral slurry composed of particulate material of known or unknown composition suspended in a fluid matrix. The ultrasonic energy passes through the slurry stream and is attenuated by a factor proportional to the size of the particles in the stream, as well as other factors. The amplitude of the pulses leaving the stream may then be measured to provide a measure of the attenuation produced by the stream, and consequently an indication of the size of the particles in the stream.

The present invention is directed to an improved method and apparatus for measuring the amplitude of the envelope produced by a series of successively occurring electrical pulses produced in this manner. It will be understood, however, that the present invention also has application to any situation where it is desirable to accurately measure the envelope produced by a string of successively occurring electrical pulses.

In a preferred embodiment, the electrical pulses are passed through a precision attenuator which provides a means for calibrating the apparatus as will be explained in more detail hereinafter. The attenuated pulses are applied to the input of a variable gain amplifier, the gain of which may be adjusted electronically by a control signal of digital origin. The amplified pulses are applied to a peak detector which samples and holds the peak amplitude of the amplified pulse.

The peak amplitude of the pulse is compared with a fixed reference voltage. A digital latch is set or reset depending on whether the peak amplitude of the pulse is greater or less than the reference voltage.

The output from the digital latch is applied to a digital processor which uses the latch data to modify the contents of a twelve bit successive approximation register. The contents of the register is used to control the gain of the variable gain amplifier in such a way that the amplitude of the next successive pulse held by the peak detector will approach the value of the reference voltage.

The above described process is repeated with each successive pulse causing modification to one or more bit positions of the successive approximation register in order to adjust the gain of the variable gain amplifier in such a way that the peak amplitude of the held pulses approaches the value of the reference voltage. As each of the bit positions of the register is changed by successive pulses, the gain of the amplifier is adjusted in finer and finer increments until the amplitude of the last held pulse approximates the value of the reference voltage. At this point, the gain of the amplifier is inversely proportional to the amplitude of the pulse envelope. In addition, the contents of the successive approximation register can be so formatted that the binary number stored in this register is also proportional to the amplitude of the pulse envelope. Consequently, the binary number stored in the register may be easily used to provide an indication of the pulse envelope amplitude.

The processing of the present invention is carried out in a digital processor which may be a general purpose computer, a special purpose computer, microprocessor or the like, using a stored program implementing the iterative adjustment of the amplifier gain and modification of the contents of the successive approximation register.

Further features of the invention will become apparent from the detailed description which follows.

BRIEF DESCRIPTION OF THE DRAWING

FIG. 1 is a block diagram of the successive approximation envelope detection apparatus of the present invention.

FIG. 2 is a flow diagram illustrating the processing of the successive approximation envelope detector of the present invention.

DETAILED DESCRIPTION

The envelope detection apparatus of the present invention is illustrated in block diagram form in FIG. 1. An ultrasonic transmitter 1 provides short pulses of RF energy on line 2 to an ultrasonic transducer 3 positioned along one surface of a thin stream of particulate slurry 4. The short ultrasonic pulses are of relatively constant known amplitude and are thus directed toward the slurry 4 as at 5.

The ultrasonic pulses which pass through the slurry stream are attenuated as at 6, to a degree depending on the particle size of particles in the slurry, as well as other factors such as the specific gravity of the slurry. The attenuated pulses are received by a receiving transducer 7 and applied on line 8 to a precision attenuator 9. The precision attenuator reduces the amplitude of the pulses by a known factor for use in calibrating the detector of the present invention as will be explained in more detal hereinafter.

The attenuated pulses are applied on line 10 to the input of a variable gain amplifier 11 having a gain K established by a control signal on control line 12. Variable gain amplifier 11 may be responsive to a digital control signal or an analog control signal as is well known in the art. In the case where the amplifier is responsive to an analog signal, it will be understood that a suitable D/A converter may be provided to convert the output data signals produced by the processor as will be described in more detail hereinafter.

The amplified pulses from amplifier 11 are applied on line 13 to a peak detector 14. The peak detector establishes the maximum amplitude of the pulse and produces an output equal to this amplitude. Consequently, the signal appearing on output line 15 from peak detector 14 will be a signal having an amplitude equal to the maximum amplitude of the amplified pulse produced by variable gain amplifier 11. In some circumstances, a reset signal may be applied to peak detector 14 on line 16. In other cases, the peak detector may be self-resetting as is well understood in the art.

The pulse amplitude signal on line 15 is applied to the inverting input of a voltage comparator 17. The non-inverting input of comparator 17 is connected to a DC voltage reference 17a so as to establish a constant switching threshold. In the present invention, the voltage reference is established at +1.000 VDC. However, it will be understood that other fixed levels for the reference may be used, depending on the dynamic range of the peak detector. As will become apparent from the description which follows, the processing of the present invention attempts to adjust the gain K of variable gain amplifier 11 so that the amplitude of the pulse peak appearing on line 15 approaches the value of the voltage reference produced by reference source 17a. In the present implementation illustrated in FIG. 1, the use of a one volt reference reduces the dynamic range over which the components must work, and also eliminates erroneous results which might be caused by low level noise signals.

The output from comparator 17 is applied on line 18 to the input of a digital latch 19. In the embodiment illustrated in FIG. 1, digital latch 19 will produce a 0 bit output on DATA line 20 if the peak amplitude of the pulse on line 15 is greater than the reference voltage, i.e. 1.000 VDC. Conversely, digital latch 19 will produce a 1 bit output on data line 20 if the value of the peak signal on line 15 is less than the voltage reference. Digital latch 19 may be enabled at the appropriate point in the processing sequence by an input signal on ENABLE line 21.

As will be explained in more detail hereinafter, if a logical 0 is produced on DATA line 20, this indicates that the input to comparator 17 is too large, and that the gain K of variable gain amplifier 11 should be reduced. On the other hand, if the output on DATA line 20 is a logical 1, this indicates that the input signal to comparator 17 is too low, and that the gain K of the variable gain amplifier 11 should be increased. This processing is carried out by a digital processor, shown generally at 22, which may be a general purpose computer, a special purpose computer, a microprocessor or the like. A display/keyboard 23 may be associated with processor 22 for providing input data to the processor, and for providing a display of output information. A signal is also provided on output line 24 from processor 22 to cause ultrasonic transmitter 1 to produce RF pulses as described hereinabove.

The processing for processor 22 is illustrated in the flow diagram of FIG. 2. It will be understood that this processing may be incorporated in a suitable computer program associated with processor 22 as software, firmware or the like. Specifically, the program may be incorporated in a ROM 22a associated with processor 22.

In a preferred embodiment of the invention, a storage register 22b is established in processor 22 which may be implemented as a memory location in RAM storage. As illustrated in FIG. 1, the register has been designated as the successive approximation register (SAR) 22b. The capacity of this register will be related to the number of successive pulses required to produce the desired precision in the measurement of the pulse envelope. For purposes of an exemplary showing, a twelve bit register has been used which will result in measurement precision of ±0.1 db of the DC voltage reference 17a, i.e. 0.001 volts.

In the implementation of the present invention, it is desired that the number stored in the successive approximation register 22b at the end of the processing sequence be directly proportional to the measured amplitude of the pulse envelope. It is also desired that the apparatus be capable of measuring envelope amplitudes between 1 mv and 1.0 volts. Consequently, for purposes of an exemplary showing since the use of a twleve bit register provides a total count of 4095, each incremental count of the SAR will correspond to 0.244 mv. Thus, a register count of 4 will correspond to approximately 1 mv, while the maximum register count of 4095 will correspond to approximately one volt. In other words, the amplitude of the pulse envelope can be found by multiplying the value of the contents of the SAR by 0.000244.

It will also be observed that the value of the gain K of variable gain amplifier 11 will be inversely proportional to the amplitude of the pulse envelope as well as the contents of the SAR. Since it is desirable that the dynamic range of peak detector 14 be restricted to the region around one volt, the gain K of amplifier 11 has been chose to vary between 1 and 1000. Consequently, the gain of the amplifier will be unity when the amplitude of the envelope is 1.0 volts, and will be 1000 when the amplitude of the envelope is 1 mv. In other words, the gain K of variable amplifier 11 can be calculated approximately by dividing the maximum compacity of the SAR, i.e. 4095, by the actual number stored in the SAR register. Thus, the gain of amplifier 11 will be about 256 when the contents of register 22b is 16.

Returning to the processing of FIG. 2, SAR 22b is first set to an initial value which will produce a mid-range gain for amplifier 11. For example, if the number stored in SAR 22b is initially set to 16, the gain K of amplifier 11 will be initially 256.

A counter is also established having a capacity equal to the number of bits in the successive approximation register. Consequently, in the present embodiment, this counter will have a maximum capacity of 12. A illustrated in FIG. 2, the number in this counter N is initially set to unity.

Thereafter, peak detector 14 is reset by a suitable signal on line 16, if necessary and ultrasonic transmitter 1 is caused to produce a RF pulse by a suitable signal on line 24. The resulting pulse passes through the particulate slurry 4, and is recieved by transducer 7. The pulse is then attenuated by precision attenuator 9 and given an initial gain of 256 by amplifier 11. The peak of the pulse is detected and maintained by the peak detector, and applied to the input of the comparator, which will produce a suitable output on line 18 and cause a corresponding change of state of digital latch 19. During this sequence of events, the processing pauses to allow for the time delays through the various analog and digital elements.

After a suitable delay time, the digital latch 19 is enabled by an ENABLE signal on line 21, and the data, a logical 1 or 0 on DATA line 20, is read by processor 22.

The processing then determines whether or not latch 19 has been set. If the latch has been set, the Nth bit in the successive approximation register is reset. The next bit, i.e. the next less significant bit, is then set. However, if the latch has not been set, the processing proceeds to only set the Nth+1 bit.

A test is then made to determine if all of the bits in the successive approximation register have been addressed;

in other words, whether the value of counter N has reached a value of 12. If this is not the case, counter N is incremented and the next less significant bit is addressed in the same manner as described. However, if all the bits of the register have been addressed, i.e. the processing has proceeded to the least significant bit of the successive approximation register, the contents of the register are read and multiplied by a suitable proportionality constant to provide a direct readout of the amplitude of the pulse envelope. In the present embodiment, this constant is 0.000244 as described hereinabove. This information may then be outputted to a suitable display 23 or the like, or provided as input data to other measurement equipment.

An example of the processing of the present invention is illustrated below in Table I. For this example, it will be assumed that the amplitude of pulses received at the input to amplifier 11 is constant at 0.35 volts.

As illustrated in Table I, the contents of the successive approximation register is displayed, with the most significant bit at the far left. The values of amplifier gain are listed in the next column. The column headed Comparator Input describes the voltage level appearing at the inverting input of comparator 17, i.e. the output from peak detector 14. The next column describes the status of the N counter. The last column describes the status of digital latch 19.

Following the processing described hereinabove, the SAR is initially set to a value of 16, producing a gain value of 256. Since the input to the comparator is greater than 1, the digital latch will produce a logical 0 on DATA line 20. Since the latch is not set, the Nth+1 bit (i.e. bit 11) is set. This results in an amplifier gain of 3.938 and an input to the comparator of 1.378 volts. Since the input to the comparator is still greater than 1.000 volts, the latch remains reset, and bit 10 of the successive approximation register is set. At the third pass through the processing, the amplifier gain is 2.639, which results in an input to comparator 17 of less than 1.000 volts, so that the latch is set. This results in bit 10 of the successive approximation register being reset, and bit 9 being set. As can be seen from Table I, this processing continues until N=12. At this point, the amplifier gain K=2.858, which results in a comparator input of approximately 1.000 volts.

It will be observed that at the terminal step in the processing, the contents of the successive approximation register 22b reads $1433_{10}$. This number may be multiplied by the proportionality constant described above, i.e. 0.000244 to give the measured pulse amplitude, 0.35 volts.

It will be observed that the processing of the present invention adjusts the gain K in finer increments for each successive pulse, sometimes higher, sometimes lower, to finally force the peak amplitude of the last peak detected pulse to be within ±0.1 db of the voltage produced by voltage reference source 17a. At the end of twelve pulses, processor 22 reads the contents of the successive approximation register. The contents of the register is proportional to the relative amplitude of the pulses passing through the slurry, and therefore proportional to the attenuation of the pulses produced by the slurry itself. As a further processing step, processor 22 may convert the contents of the successive approximation register to db of attenuation of the slurry by reference to a calibration table or the like. For example, the calibration table may be derived by using the precision attenuator to simulate the attenuation caused by a slurry when the slurry stream in passing between transducers 3 and 7 is replaced by pure water. Consequently, the system is self-calibrating on water so that many measurement error sources are eliminated such as harmonic and amplitude distortion of the receiver amplifier, variation in gain settings, circuit temperature drifts, and long term component aging effects.

It will be understood that various changes in the steps, details, materials and arrangements of parts, which have been herein described and illustrated in order to explain the nature of the invention, may be made by those skilled in the art within the principle and scope of the invention as expressed in the appended claims.

For example, the successive approximation register may initially be set to any initial value to establish a starting gain for amplifier 11. In addition, as illustrated in dashed lines in FIG. 2, on successive runs through the processing, the previously established contents of the successive approximation register may be used as the starting value, rather than presetting the register to an arbitrary value such as $16_{10}$.

TABLE I

| REGISTER | K | COMPARATOR INPUT | N | LATCH |
| --- | --- | --- | --- | --- |
| 000000010000 | 256 | >1 | 1 | 0 |
| 010000010000 | 3.938 | 1.378 | 2 | 0 |
| 011000010000 | 2.639 | 0.924 | 3 | 1 |
| 010100010000 | 3.160 | 1.106 | 4 | 0 |
| 010110010000 | 2.876 | 1.007 | 5 | 0 |
| 010111010000 | 2.753 | 0.963 | 6 | 1 |
| 010110110000 | 2.813 | 0.985 | 7 | 1 |
| 010110010000 | 2.876 | 1.007 | 8 | 0 |
| 010110011000 | 2.860 | 1.001 | 9 | 0 |
| 010110011100 | 2.852 | 0.998 | 10 | 1 |
| 010110011010 | 2.856 | 1.000⁻ | 11 | 1 |
| 010110011001 | 2.858 | 1.000⁺ | 12 | — |

The embodiments of the invention in which an exclusive property or privilege are claimed are as follows:

1. Apparatus for measuring the amplitude of a train of successively occurring electrical signals comprising:
   amplifier means for receiving said signals having a variable gain established by a control signal;
   reference means establishing a reference voltage;
   means for successively comparing the amplitude of each of said signals from said amplifier means with said reference voltage; and
   means responsive to said comparison means for producing said control signal so as to adjust the gain of said amplifier means such that the amplitude of signals from said amplifier means approaches said reference value, said control signal being representative of the amplitude of said electrical signals, said control signal producing means comprising a successive approximation storage register having a plurality of individually addressable bits and means responsive to said comparison means for successively setting or resetting no more than one of said bits for each of said successively occurring electrical signals, and means for deriving said control signal from the contents of said register.

2. The apparatus according to claim 1 wherein said reference voltage comprises a DC voltage.

3. The apparatus according to claim 1 wherein said processor means is operative to hold the gain of said amplifier means constant for the duration of said electrical signal, said control signal producing means operating to change the gain of said amplifier means following termination of said electrical pulse and before the occurrence of a subsequent electrical pulse.

4. The apparatus according to claim 3 including means for measuring the peak amplitude of said electrical signal, said comparison means including means for comparing said peak amplitude to said reference voltage, and means for strobing said comparison means output into said register.

5. The apparatus according to claim 1 including means for determining the peak amplitude of said pulses.

6. The apparatus according to claim 5 wherein the value of the contents of said register is proportional to the amplitude of the envelope of said pulses.

7. The apparatus according to claim 6 wherein said peak amplitude determining means comprises a peak detector connected between said amplifier means and said comparison means.

8. The apparatus according to claim 7 wherein said processor means includes counter means for counting the number of pulses measured by said apparatus, said counter having a maximum count equal to the number of bits in said register.

9. The apparatus according to claim 8 wherein said setting or resetting means comprises means for adjusting the gain of said amplifier means in decreasing increments with successively occurring pulses.

10. The apparatus according to claim 9 wherein said setting or resetting means comprises means for increasing the value of the contents of said register if the amplitude of pulses from said peak detector is greater than said reference voltage and decreasing the value of the contents of said register if the amplitude of pulses from said peak detector is less than said refernece voltage.

11. The apparatus according to claim 10 wherein said processor means includes means for setting a single bit if the amplitude of pulses from said peak detector is greater than said reference voltage, and for resetting a bit and setting an adjacent less significant bit if the amplitude of pulses from said peak detector is less than said reference voltage.

12. The apparatus according to claim 11 wherein said processor means includes means for setting some at least of said bits of said register to establish an initial gain setting for the first one of said pulses.

13. Apparatus for measuring the amplitude of an envelope produced by N successively occurring electrical pulses comprising:

an amplifier having a variable gain established by a control signal;
peak detector means connected to the output of said amplifier for establishing the peak amplitude of each pulse;
means establishing a DC reference voltage;
voltage comparator means responsive to said peak detector for comparing the peak amplitude of each pulse with said reference voltage; and
digital processor means responsive to said comparator for producing said control signal, including a storage register having a capacity of N bits, each of said bits corresponding to one of said N pulses, means for setting or resetting each of said bits in turn dependent on whether the peak amplitude output from said peak detector for the corresponding pulse is greater or less than said reference voltage, and means for using the contents of said register to generate said control voltage, such that the gain of said amplifier is adjusted in decreasing increments with successively occurring pulses, the value of the contents of said register being representative of the amplitude of said envelope.

14. The apparatus according to claim 13 wherein said processor means includes means for setting the Nth bit of said register if the peak amplitude output from said peak detector for the Nth pulse is greater than said reference voltage and for resetting the Nth bit and setting the adjacent less significant bit if the peak amplitude output from said peak detector for the Nth pulse is less than said reference voltage.

15. The apparatus according to claim 14 wherein said processing means includes means for setting the contents of said register to a predetermined number representative of a predetermined amplifier gain.

16. The apparatus according to claim 15 wherein the number stored in said register following the Nth pulse is proportional to the amplitude of said envelope.

17. The apparatus according to claim 15 wherein the gain of said amplifier following the Nth pulse is inversely proportional to the amplitude of said envelope.

18. In a system for measuring the size of particles in a fluid slurry stream of the type measuring the attenuation of RF pulses passing through the slurry comprising an ultrasonic transmitter for producing RF pulses of predetermined amplitude, a transmitting transducer responsive to said transmitter adjacent one surface of the slurry stream, and a receiving transducer adjacent the opposite surface of the slurry stream for receiving pulses passing through the slurry, the improvement in combination therewith comprising means for measuring the amplitude of the envelope produced by N successively occurring received pulses including:

an amplifier having a variable gain established by a control signal responsive to said received pulses;
peak detector means connected to the output of said amplifier for establishing the peak amplitude of each pulse; means establishing a DC reference voltage;
voltage comparator means responsive to said peak detector for comparing the peak amplitude of each pulse with said reference voltage; and
digital processor means responsive to said comparator for producing said control signal, including a storage register having a capacity of N bits, each of said bits corresponding to one of said N received pulses, means for setting or resetting each of said bits in turn dependent on whether the peak amplitude output from said peak detector for the corresponding received pulse is greater or less than said reference voltage; and means for using the contents of said register to generate said control voltage, such that the gain of said amplifier is adjusted in decreasing increments with successively occurring received pulses, the value of the contents of said register being representative of the amplitude of said envelope.

19. The apparatus according to claim 18 including means for calculating the attenuation of said slurry stream using the amplitude of transmitted pulses and the amplitude of said envelope.

20. The apparatus according to claim 19 including a precision attenuator positioned between said receiving transducer and said amplifier.

* * * * *